United States Patent
Odell et al.

(10) Patent No.: US 6,263,641 B1
(45) Date of Patent: Jul. 24, 2001

(54) METHOD AND APPARATUS FOR MANUFACTURING, FILLING AND PACKAGING MEDICAL DEVICES AND MEDICAL CONTAINERS

(75) Inventors: Robert B. Odell, Franklin Lakes; Donald J. Porfano, Hackensack, both of NJ (US); James C. Kropatsch, Columbus, NE (US); Jorge J. Campos, edo de Mexico; Mario de Aguero Servin, Mexico City, both of (MX); Patrick G. Carre, La Buisse (FR); Mark A. German, Columbus, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/678,080

(22) Filed: Oct. 3, 2000

Related U.S. Application Data

(63) Continuation of application No. 09/267,107, filed on Mar. 12, 1999, now Pat. No. 6,189,292.
(60) Provisional application No. 60/077,897, filed on Mar. 13, 1998, and provisional application No. 60/102,338, filed on Sep. 29, 1998.

(51) Int. Cl.[7] .................................................... B65B 55/02
(52) U.S. Cl. ............................... 53/425; 53/426; 53/471; 53/473; 53/489
(58) Field of Search ............................ 53/425, 420, 452, 53/471, 487, 490, 443; 65/36; 141/1; 422/28

(56) References Cited

U.S. PATENT DOCUMENTS

| | | |
|---|---|---|
| 4,521,237 | 6/1985 | Logothetis . |
| 4,628,969 | 12/1986 | Jurgens et al. . |
| 4,718,463 | 1/1988 | Jurgens, Jr. et al. . |
| 5,141,430 | 8/1992 | Maus et al. . |

(List continued on next page.)

FOREIGN PATENT DOCUMENTS

| | | |
|---|---|---|
| 19622283 | 11/1997 | (DE) . |
| 0227401 | 10/1991 | (EP) . |
| 0553926 | 8/1993 | (EP) . |

(List continued on next page.)

OTHER PUBLICATIONS

"Clean Room Injection Moulding" Eckardt, Plast Europe, Mar. 1992, pp. 54–55.
"Disposable Syringes: Klockner Standards for Mass Production", Plastics Southern Africa PSA Sep. 1991, vol. 21, No. 5, p. 10.
"Getting Started in Medical Plastics" European Plastics News, Oct. 1991, vol. 18, No. 8 pp. 24–25.
"Disinfection and Sterilization" Sykes, $2^{nd}$ Edition, Chapman and Hall Ltd.
"Cleanroom Design" Whyte, Publ. John Wiley & Sons, 1991.

Primary Examiner—Peter Vo
Assistant Examiner—Louis K. Huynh
(74) Attorney, Agent, or Firm—Allen W. Wark

(57) ABSTRACT

Clean syringe barrels from forming device immediately transferred to a controlled environment to maintain a clean work area. The work area can be a clean room or localized area to avoid the need to maintain cleanliness levels in an entire room. A localized area uses a housing assembly having a HEPA filter coupled to an air inlet to filter the air entering the housing. An air blower is coupled to the air inlet to feed filtered air into the housing assembly and to maintain a positive air pressure in the housing assembly to prevent unfiltered outside air from entering. Syringe tip closures can be introduced into the housing assembly, where syringe barrels and tip closures are cleaned with filtered ionized air and the tip closures are coupled to the barrels. A thin coating of lubricant is applied to the inner surfaces of the syringe barrels. The syringe barrels or medical container can be filled with a substance and a closure member is attached. While still in the housing assembly the syringe barrels can be formed into an array and placed in a clean outer container. The outer container is then closed and sealed. The outer container and syringe barrels can be sterilized with heat, radiation or by exposure to a sterilizing gas.

29 Claims, 8 Drawing Sheets

U.S. PATENT DOCUMENTS

| | | |
|---|---|---|
| 5,597,530 | 1/1997 | Smith et al. . |
| 5,620,425 | 4/1997 | Heffernan et al. . |
| 5,687,542 | 11/1997 | Lawecki et al. . |

FOREIGN PATENT DOCUMENTS

| | | |
|---|---|---|
| 0555900 | 8/1993 | (EP) . |
| 0556034 | 8/1993 | (EP) . |
| 0709105 | 5/1996 | (EP) . |
| 0741080 | 11/1996 | (EP) . |
| 0815884 | 1/1998 | (EP) . |
| 94928996 | 1/1998 | (EP) . |
| 0849173 | 6/1998 | (EP) . |
| 9413328 | 6/1994 | (WO) . |
| 9413345 | 6/1994 | (WO) . |
| 9512482 | 5/1995 | (WO) . |
| 9613289 | 5/1996 | (WO) . |
| 9618541 | 6/1996 | (WO) . |
| 9628201 | 9/1996 | (WO) . |
| 9708054 | 3/1997 | (WO) . |
| 9744068 | 11/1997 | (WO) . |
| 9805366 | 2/1998 | (WO) . |
| 9819715 | 5/1998 | (WO) . |
| 9833705 | 8/1998 | (WO) . |

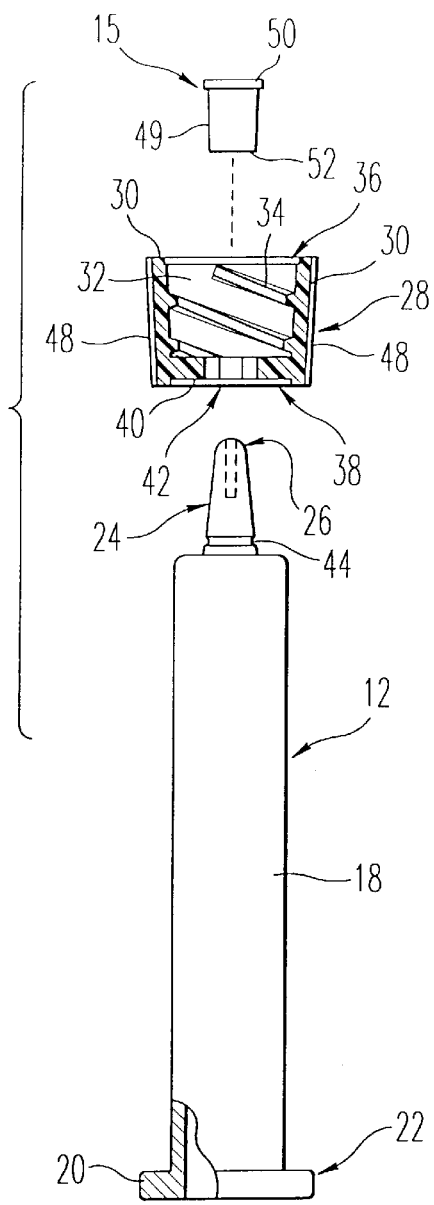
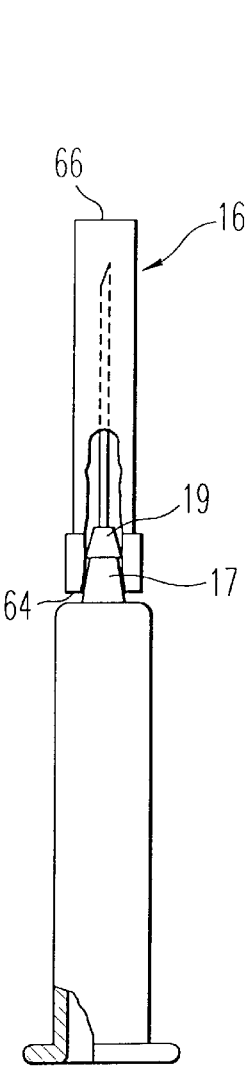
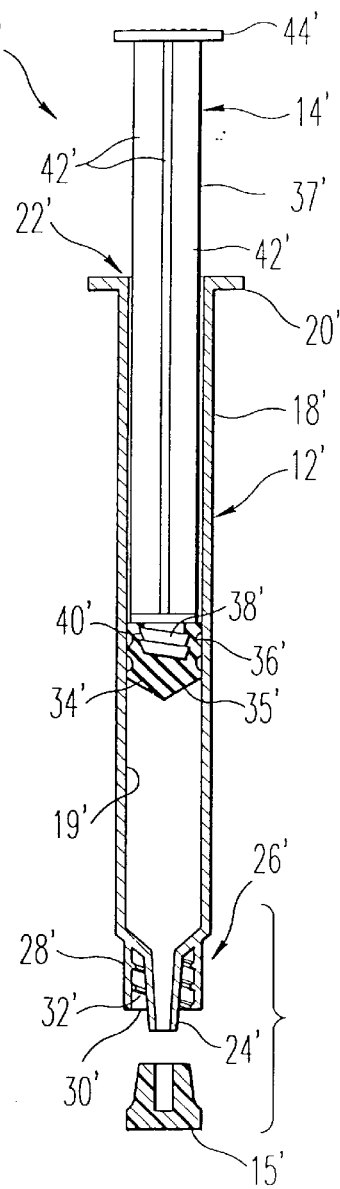
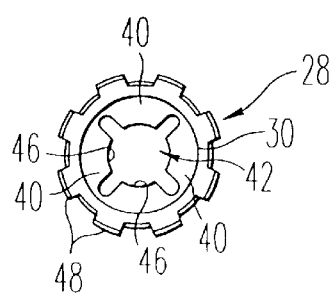
FIG. 1
FIG. 3
FIG. 4
FIG. 2

METHOD AND APPARATUS FOR MANUFACTURING, FILLING AND PACKAGING MEDICAL DEVICES AND MEDICAL CONTAINERS

CROSS-REFERENCE TO RELATED APPLICATION

This application is a continuation of application Ser. No. 09/267,107 filed Mar. 12, 1999 now U.S. Pat. No. 6,189,292, which claims the benefit under 35 U.S.C. § 119(e) of U.S. provisional application Serial No. 60/077,897 filed Mar. 13, 1998 and U.S. provisional application Serial No. 60/102,338 filed Sep. 29, 1998, which are hereby incorporated by reference in their entirety.

FIELD OF THE INVENTION

The present invention relates generally to a method of manufacturing drug delivery and drug container devices, such as syringe components, and packaging the components in a clean, substantially particulate-free area. More particularly, the invention is directed to a method for manufacturing glass or plastic syringe barrels and assembling and packaging the syringe barrels in a clean room or locally controlled environment which is clean and substantially free of airborne particulates.

BACKGROUND OF THE INVENTION

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, the drug delivery devices are packaged and sterilized.

Syringes have been classified into several general types. The first type is assembled and placed in sterile packaging which can be shipped with a vial or ampoule of a drug or other injectable solution. The vial or ampoule is generally made of glass or other clear material that does not interfere with the stability of the drug during prolonged storage. The syringe is filled with the drug or other solution at the point of use and injected into the patient. Another type of syringe is packaged with a vial filled with a powdered or lyophilized drug which is dissolved in water or other suitable solvent prior to charging into the syringe.

These syringes have the disadvantage of increasing the time and difficulty of filling the syringe at the point of use with increased possibility of contamination of the syringe and/or drug solution. There is a further risk of glass particles from the ampoules contaminating the drug solution when the ampoules are opened.

Several of these disadvantages are overcome by providing prefilled syringes which can be filled with a suitable drug solution prior to use. Prefilled syringes, as the term is known in the art, are syringes that are filled by the drug manufacturer and shipped to the health care provider ready for use. Prefilled syringes have the advantage of convenience and ease of application with reduced risk of contamination of the drug solution. A difficulty in producing prefilled syringes, if they are made of plastic rather than glass, is selecting suitable materials that maintain their clarity for extended periods of time and do not contaminate or react with the drug solution.

Syringes and other drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases.

Various operations are able to form clean and sterile drug delivery devices. However, subsequent handling, filling and printing of the drug delivery device can contaminate the device. It is then necessary to clean and sterilize the drug delivery device before use.

Accordingly, there is a continuing need in the industry for an improved system for manufacturing and assembling clean and sterile medical devices and filling such devices.

SUMMARY OF THE INVENTION

The present invention is directed to a method and apparatus for maintaining a clean environment during the manufacture and assembly of medical devices such as drug delivery devices and medical container devices. More specifically, the invention is directed to the manufacture of various medical containers, drug delivery and drug container devices which are clean and have a low bio-burden or are sterile at the completion of the manufacturing step and immediately transferring the devices to a clean room or to a locally controlled environment to maintain cleanliness levels while assembling and packaging the devices. The medical devices can be filled with a suitable substance such as, saline solutions, flush solutions or contrast agents, pharmaceutical agents and vaccines, in either a dry or liquid state.

Accordingly, a primary object of the invention is to manufacture medical container devices immediately upstream of at least one housing assembly which defines a locally controlled environment. The medical containers are manufactured from glass or plastic under conditions which produce a substantially clean and sterile part. The housing assembly receives the medical containers directly from the manufacturing apparatus without a prior cleaning step so that the containers can be assembled within the housing assembly under controlled conditions to maintain predetermined cleanliness standards for medical containers and devices.

Another object of the invention is to provide a method for manufacturing a substantially clean and low bio-burden medical containers, such as a syringe barrel and assembling the syringe barrel with various components, such as a tip closure or Luer lock, in a locally controlled environment without the need for a water washing step.

A further object of the invention is to provide a method and apparatus for forming glass medical containers, such as drug delivery devices or components, annealing the glass medical containers, and then immediately capturing the annealed container in an environmentally controlled area to maintain a predetermined cleanliness and low bio-burden. The annealed glass medical containers are captured from the annealing oven in a manner to maintain the cleanliness and low bio-burden to avoid a mandatory cleaning step. The environmentally controlled area can be a clean room or a locally controlled environment.

Another object of the invention is to provide a method and apparatus for producing clean medical containers and delivering the devices to a housing assembly which defines a locally controlled environment, where the housing assembly includes a HEPA filter and a fan or blower to feed filtered air into the housing and maintain the housing assembly at predetermined cleanliness levels.

In embodiments of the invention, the medical containers are glass syringe barrels, and particularly prefillable glass syringe barrels, manufactured by processes which produce substantially clean and low bio-burden or sterile syringe barrels. The glass syringe barrels are made from cylindrical glass tubes that are cut to a desired length. The tubes are then fed to a forming machine which in one embodiment heats the ends of the tubes and forms a flange at one end and a tip at the opposite end. The glass syringe barrels are annealed by heating in a Lehr or annealing oven to at least about 560° C. for an appropriate time to relieve stresses in the glass. The annealing produces a clean and low bio-burden syringe barrel which is then immediately transferred to an environmentally controlled area substantially without contamination.

A further object of the invention is to provide a housing assembly which maintains a locally controlled environment for assembling medical containers and packaging an array of medical containers in closed second containers. The medical containers can be sterilized in a subsequent step.

The housing assembly defining the locally controlled environment can be a portable unit having a work surface for performing the desired operations manually or automatically. The work surface is enclosed by side panels, at least some of which are preferably transparent to allow viewing and inspection by an operator located outside the housing. The assembly includes a top wall coupled to the side panels to define an enclosure. The assembly includes a fan or blower assembly and a filter assembly to direct filtered air into the housing and maintain a clean environment and can be operated to maintain a positive pressure in the housing assembly to prevent the infiltration of unfiltered air. An optional exhaust fan can also be provided to draw air downwardly through the housing assembly and exhaust the air without causing a negative pressure in the housing assembly.

In one embodiment of the invention, the medical containers exit the forming device and are immediately captured in an environmentally controlled area to maintain cleanliness. The medical devices, such as syringe barrels, in the housing assembly optionally can be cleaned by streams of clean filtered air or ionized air when necessary. The cleaning air removes substantially all particulates that may be adhered to the inner and outer surfaces of the barrel to attain the desired cleanliness level. A vacuum exhaust can be provided in the area of the barrel to carry the particulates away from the barrel and out of the housing assembly. Tip closures, Luer locks or syringe needles with their associated needle sheaths are also supplied to the housing assembly where they can be cleaned with filtered air or ionized air. The tip closures, Luer locks and needles are coupled to the syringe barrels. A lubricant is preferably applied to the inner surface of the syringe barrel, and the syringe barrels are placed in a grid or tray which is in turn placed in a container such as a tub. A plastic sheet is placed over the tray and the tub is closed with a sheet of flexible material which generally is heat-sealed to the tub. The tub is then enclosed in an outer wrap such as a plastic bag which is heat sealed. The tub, outer wrap and contents are sterilized by a sterilizing gas or radiation. Some or all of these operations can be conducted in a single housing assembly or in a plurality of housing assemblies coupled together.

A method of producing prefillable, glass syringe barrels in accordance with the present invention comprises the steps of supplying a glass tube to a forming device and forming a hollow syringe barrel having a flange at one end and a tip at the other end. The syringe barrels are annealed in a Lehr oven, cooled, and received in a first housing assembly having an air filtering device to maintain a predetermined cleanliness level therein, and a plurality of tip closures are supplied to the first housing assembly and are assembled with the syringe barrels. A stream of filtered air is directed to the syringe barrels and syringe components to remove particulates therefrom and clean the outer surfaces thereof. The assembled syringe barrels and syringe components are conveyed to a second housing assembly having a filtering device for maintaining a predetermined cleanliness level, and a lubricant is preferably applied to the inner surfaces of the syringe barrels. In a third housing assembly, the syringe barrels are formed into an array and placed into a container having a closed bottom, side walls and an open top. Thereafter, the container is conveyed to a fourth housing assembly having an air filtering device to maintain a predetermined cleanliness level, and a closure is applied to the container to seal the container.

The aspects of the invention are further attained by providing a method of producing a filled syringe comprising the steps of forming a plastic syringe barrel in an injection molding machine where the syringe barrel has a cylindrical side wall, an open proximal receiving end and a frustoconically shaped outlet nozzle at its distal end and transferring the syringe barrel, without any additional cleaning or sterilization, into an environmentally controlled area to maintain a predetermined cleanliness level. A stream of filtered air is directed toward the syringe barrel in the environmentally controlled area to remove particles from surfaces thereof to clean the syringe barrel. A tip cap is delivered to the environmentally controlled area and the tip cap is assembled onto the outlet nozzle of the syringe barrel to close the outlet nozzle and the syringe barrel is filled with a substance through its open proximal end. A stopper is delivered to the environmentally controlled area and is inserted into the open proximal end of the barrel to form a prefilled syringe. The prefilled syringe is then removed from the environmentally controlled area. In further embodiments, a stopper is applied to the syringe followed by filling the syringe through the tip or nozzle and then closing with a tip cap.

These and other aspects, advantages and salient features of the invention will become apparent to one skilled in the art from the annexed drawings and the following detailed description which discloses preferred embodiments of the invention.

BRIEF DESCRIPTION OF THE DRAWINGS

Referring to the drawings which form a part of this original disclosure:

FIG. 1 is an exploded side elevational view of a glass syringe showing the Luer locking collar;

FIG. 2 is an end view of the Luer locking collar of FIG. 1;

FIG. 3 is a side elevational view of an assembled syringe barrel in an embodiment of the invention;

FIG. 4 is a side elevational view of a plastic syringe in a further embodiment;

DETAILED DESCRIPTION OF THE PREFERRED EMBODIMENTS

Figure 5:
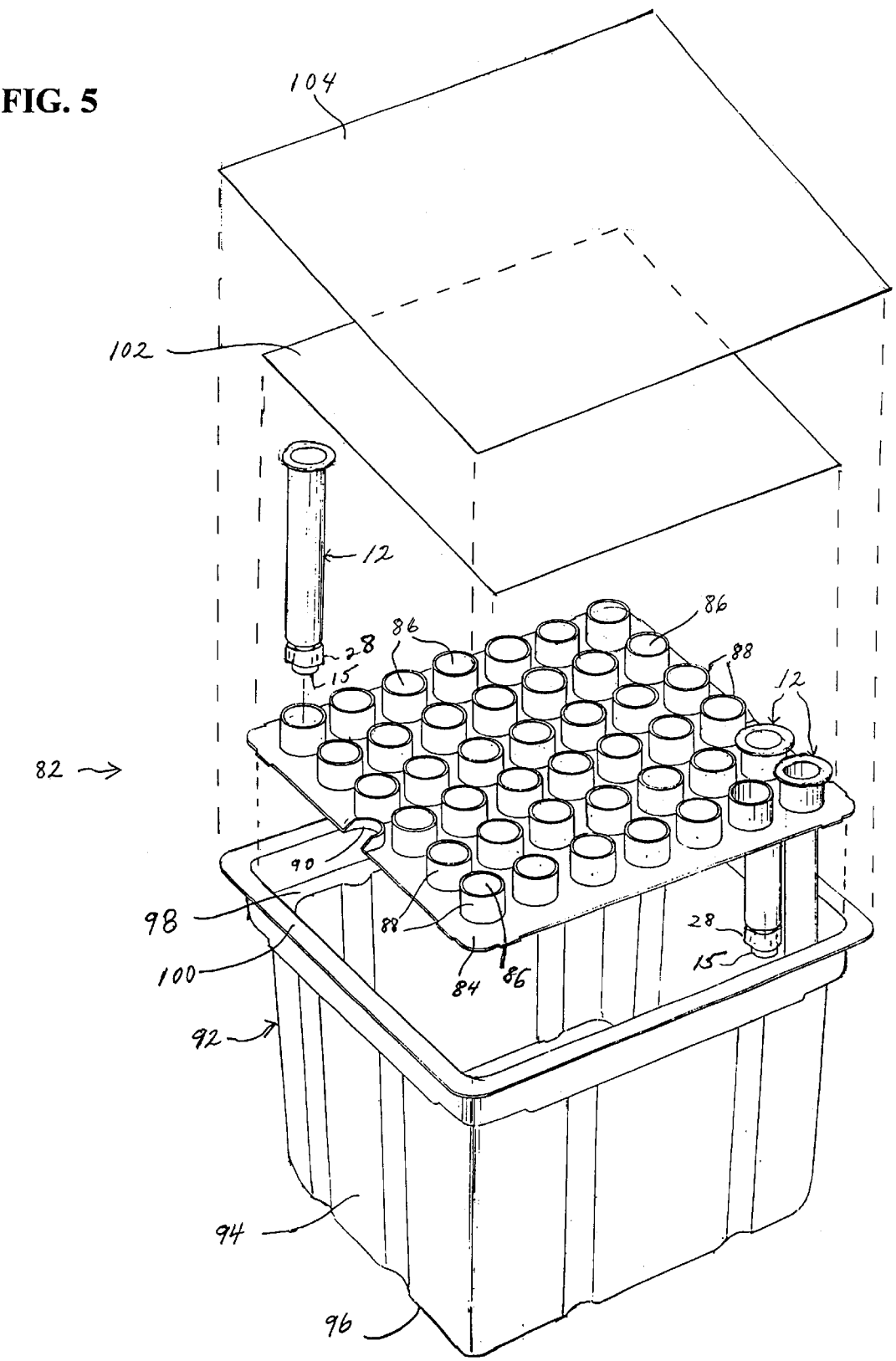
FIG. 5 is an exploded perspective view of a syringe barrel tub enclosure in an embodiment of the invention.

The present invention is directed to a method and apparatus for manufacturing and thereafter assembling and packaging medical containers, drug delivery devices and drug containers, such as vials, syringe barrels and prefilled syringes, in a clean, environmentally controlled area. As used herein, medical containers for containing and/or dispensing substances include vials and injection devices such as syringes. In addition, as used herein, a substance includes, for example, water, saline solutions, flush solutions and contrasting agents, pharmaceutical agents and vaccines in either a dry state or liquid state. The medical containers can be syringe barrels formed from a base material such as glass or plastic. The syringe barrels are used to assemble a syringe 10 as shown in FIG. 1. Although embodiments of the invention are disclosed as a hypodermic syringe assembly, it is within the purview of the present invention to include various other drug containers, such as plastic or glass cylindrical reservoirs having resilient stoppers and/or closures at one or both ends, or other drug delivery devices or appliances which require a clean environment during manufacture or assembly.

Referring to FIGS. 1 and 2, the medical container is a syringe 10 including a glass syringe barrel 12, a plastic plunger rod and attached rubber stopper or piston (not shown) and a tip closure 15 or needle sheath closure 16. In further embodiments, the syringe can be a needleless syringe as known in the art. Syringe barrel 12 in the embodiment illustrated has a cylindrical side wall 18, a flange 20 at a receiving end 22, and a frustoconical outlet nozzle 24 at a discharge end of a barrel tip 26. A Luer locking collar 28 encircles the outlet nozzle 24 to define an annular space 30 surrounding the outlet nozzle 24. Side wall 18 can include suitable printed indicia for indicating the volume of the syringe, the name of the manufacturer and the like.

Luer locking collar 28 is generally a plastic collar that is able to be snapped onto the nozzle 24 of the syringe barrel tip 26. As shown in FIGS. 1 and 2, Luer locking collar 28 includes an annular sleeve 30 having an inner wall 32 with internal threads 34. The annular sleeve 30 has an open end 36 for coupling with an externally threaded member. The sleeve 30 further has a base end 38 with a plurality of flexible tabs 40 extending radially inwardly toward the center axis of the sleeve 30 to define an opening 42. The tabs 40 are sufficiently flexible to deflect out of the plane of the tabs along an axial direction to snap into a recess 44 on the tip 26 of the syringe barrel 12. In the embodiment illustrated, four tabs 40 are included which are spaced apart around the sleeve 30 by radial gaps. The inner edges 46 of the tabs 40 have an arcuate shape complimenting the shape of the syringe barrel tip 26. The outer surface of the sleeve 30 includes longitudinal ribs 48 for gripping and rotating the Luer locking collar 28 with respect to the syringe barrel 12.

Although the syringe barrel illustrated in this embodiment includes a locking Luer-type collar 28, it is within the purview of the present invention to include syringe barrels without a collar, syringe barrels having an eccentrically positioned nozzle, and various other nozzle-like structures adapted to accept, either permanently or removably, a needle cannula or needle cannula assembly. It is only required that there is an aperture on the distal end of the syringe barrel in fluid communication with the interior of the syringe barrel. In addition to the tip closure and needle closure illustrated in this embodiment, it is also within the purview of the present invention to include a wide variety of closures for sealing a syringe barrel or drug container including, but not limited to, cannula occluding plugs, removable seals attached by adhesive or heat sealing, threaded closures and the like. In further embodiments, the syringe barrel is a cylindrical tube having plastic components attached to each end forming a thumb flange and a nozzle, respectively.

A plunger rod and a stopper or piston can be provided for assembling with the syringe barrel to manufacture prefilled syringe barrels. The stopper is typically made of a molded flexible material, such as rubber, that is sufficiently pliable and flexible to readily conform to the inner surface of the syringe barrel and form a fluid tight seal. The plunger rod is typically made of plastic.

Tip closure 15 is dimensioned to close the frustoconical nozzle 24 of syringe barrel 12. Referring to FIG. 1, tip closure 15 has a slight frustoconical sleeve 49 with a closed end 50 and an outer annular flange 52. Sleeve 49 is dimensioned to fit securely over frustoconical nozzle 24. Tip closure 15 is typically made from flexible rubber-like materials, rigid materials or peelable strip materials as known in the art.

Referring to FIG. 3, a further embodiment includes a glass syringe barrel 13 having a tapered outlet nozzle tip 17 with an enlarged end 19, a side wall 21 and a flange 23. A protective plastic needle sheath 16 has an open end 64 for coupling with syringe tip 17 and a closed end 66 opposite open end 64. Protective sheath 16 has a hollow, substantially cylindrical shape and can be dimensioned to receive a needle 60. In the embodiment illustrated, sheath 16 contacts and closes off the tip of needle 60 to prevent fluid leakage. In further embodiments, the side walls 68 are spaced from needle 60 so that sheath 62 does not contact needle 60. The needle 60 can be a stainless steel needle secured in the tip 17 by a suitable adhesive as known in the art.

FIG. 4 illustrates an embodiment where the medical container is a syringe 10' including a plastic syringe barrel 12', a plastic plunger 14' and a plastic tip closure 15' . In further embodiments, syringe 10' can be a needleless syringe or include a needle tip closure as known in the art. Syringe barrel 12' has a cylindrical sidewall 18', a flange 20' at a receiving end 22', and a frustoconical outlet nozzle 24' at a discharge end 26'. Collar 28' encircles the outlet nozzle 24' to define an annular space 30' surrounding the outlet nozzle 24'. An inner surface of collar 28' includes a threaded portion 32'. Sidewall 18' can include suitable printed indicia for indicating the volume of the syringe, the name of the manufacturer and the like.

Plunger 14' includes a molded flexible stopper 34' having a frustoconical end face 35', and a plurality of annular ridges 36' dimensioned to form fluid tight contact with the inner surface 19' of sidewall 18' of syringe barrel 12'. A plunger rod 37' includes in threaded member 38' which is coupled to an internally threaded recess 40' in stopper 34'. Plunger rod 36' has four vanes 42' extending outwardly from a center longitudinal axis and extending at substantially right angles to each other and at a flat plate 44' for pushing the plunger rod 37' through syringe barrel 12'.

Referring to FIG. 5, a plurality of syringe barrel assemblies 12 are placed in a container or tub package 82. In the embodiment illustrated, the syringe assemblies include a syringe barrel 12, a Luer locking collar 28 and a tip cap 15. In further embodiments, the syringe barrel assemblies can include a needle cannula and sheath as shown in FIG. 3. The syringe barrel assemblies can be placed in any suitable package or container depending on the particular syringe and its end use. A tray 84 is provided having a plurality of spaced-apart openings 86 and collars 88 extending upward for supporting the syringe barrels 12. In the embodiment illustrated, openings 86 and collars 88 are arranged in a series of rows and columns and are uniformly spaced apart. Tray 84 includes cut-out portions 90 for lifting and easily gripping the tray 84 and to orient the tray during various processing and filling operations. Tray 84 is nested in a suitable container such as a tub 92. Tub 92 includes side walls 94 and a bottom wall 96. A stepped portion 98 of tub 92 is formed in side walls 96 to support tray 84 so that the ends of syringe barrels 12 can be spaced from bottom wall 96. In other embodiments, the ends of syringe barrels can contact bottom wall 96. A peripheral flange 100 extends outward from the open top end of side walls 94. Tub 92 is typically an integrally formed rigid plastic unit made by a suitable molding process, such as injection molding, vacuum forming or blow molding.

Tray 84 supports an array of syringe barrels 12 and is positioned in tub 92. A protective layer of sheet material 102, such as polyethylene, foam or other plastic, is positioned to cover tray 84 and the syringe barrels 12. Preferably, sheet 102 is substantially the same size as tray 84. A closure or cover sheet 104 is then positioned on peripheral flange 100 and is sealed on the flange to completely enclose the array of syringe barrels 12. The tub 92 is then enclosed in a sealed plastic bag or wrapper. Typically, the cover sheet 104 is a thermoplastic material that is heat-sealed to flange 100 to form a complete seal. A suitable cover sheet 104 is a gas-permeable material such as a spun bonded polyolefin sold under the trademark TYVEK by E.I. DuPont & Co. This allows the syringe barrels 12 to be gas sterilized, if desired, while they are in the sealed tub 92. In further embodiments, the syringe barrels can be sterilized by radiation.

The syringe of FIGS. 1–4 can be assembled by the manufacturer and packaged in suitable clean and sterile packaging. The syringes may be packaged individually or in bulk. One example of bulk packaging places a plurality of the syringe barrels laying flat in a molded tray. A plurality of the trays are stacked in a carton which is then closed and sterilized. In embodiments of the invention, the syringe components are partially assembled so that prefilled syringes can be produced by the customer, such as a pharmaceutical manufacturer or contract filler. An object of the invention is to provide a method for manufacturing prefillable syringe components for filling with a substance and for assembling the barrels and tip closures of the syringes.

Syringe barrels 12 can be manufactured using various plastic or glass forming techniques as known in the art. Plastic medical containers can be made by conventional injection molding devices from polyolefins such as polypropylene. Although syringe barrels and other components can be manufactured using molding or forming techniques that produce low bio-burden or sterile components, subsequent handling of the components often results in contamination that requires additional cleaning and sterilization. The present invention avoids this problem.

Syringe barrels 12 in embodiments of the invention are made of glass. The glass syringe barrels are formed and annealed and then captured in a clean, locally controlled environment or clean room immediately upon being ejected or discharged from the annealing oven to maintain the syringe barrels in a substantially clean condition having low bio-burden. Glass and molded plastic drug containers and syringe barrels are typically molded at sufficient temperatures and conditions to produce clean and low bio-burden devices. The clean and low bio-burden syringe barrels are captured in an enclosed housing assembly to maintain cleanliness and low bio-burden without exposing to unfiltered air and contaminants.

Figure 6:
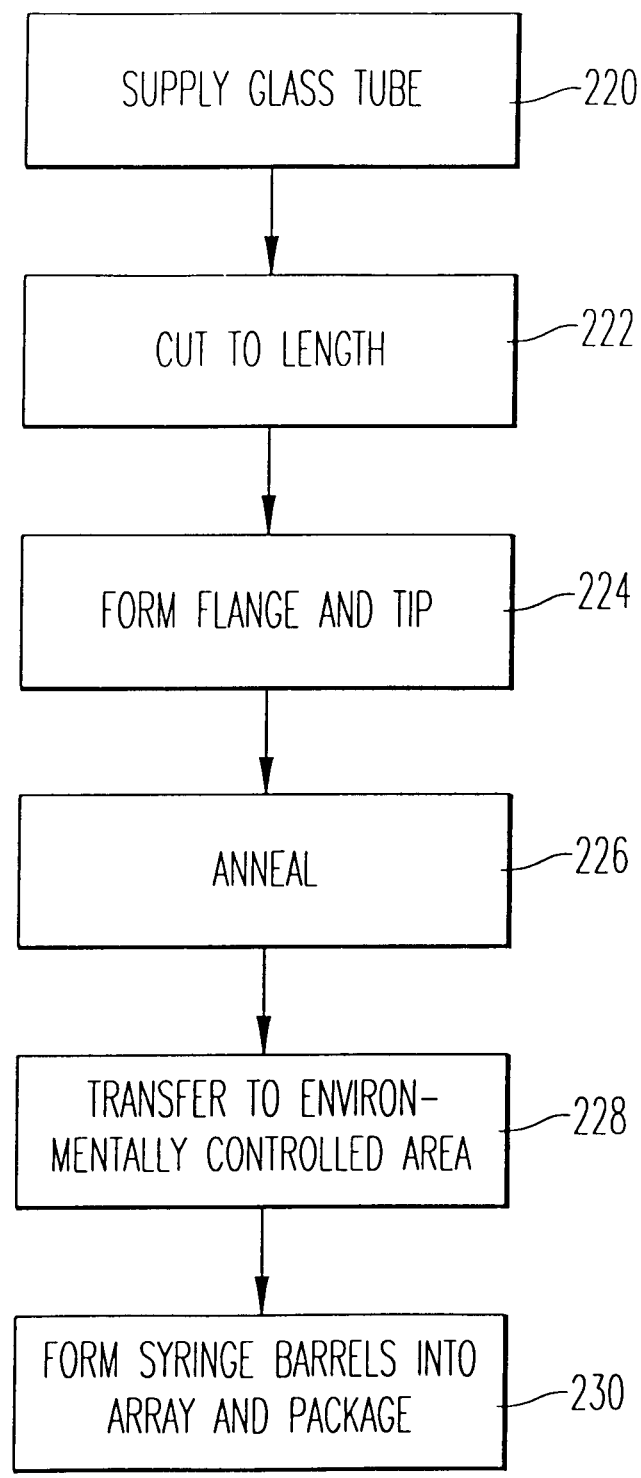
FIG. 6 is a flow chart of the manufacturing steps for forming glass syringe barrels.

The glass syringe barrels are manufactured by the steps as shown in the flow chart of FIG. 6 using standard glass forming techniques and equipment. Referring to FIG. 6, a glass tube or "cane" having a working length and a diameter corresponding to the diameter of the finished syringe barrel is provided from a supply indicated in block 220. The glass tubes can be heated in a Lehr oven of at least about 560° C. for an appropriate length of time to anneal the glass, although annealing is generally not necessary at this stage. The glass tubes are then cut to a working length as indicated in block 222 and are fed to a syringe barrel forming device. The syringe barrel forming device heats the ends of the glass tube to a softening temperature and forms a thumb flange at the proximal end and an outlet nozzle tip at the distal end as indicated in block 224. The temperature of the glass during the tip and flange formation is generally about 760°–1100° C. The formed glass syringe barrels are then heated in a Lehr oven to at least about 560° C. for an appropriate length of time to anneal the glass and relieve stresses in the syringe barrel as indicated in block 226. The length of time for the annealing is dependent on the particular glass being used and the annealing temperature as known by those skilled in the art. Thereafter, the syringe barrels are cooled and immediately transferred to a clean environment for maintaining a clean and low bio-burden condition as indicated in block 228. Alternatively, the annealed syringe barrels can be cooled in the clean environment. The syringe barrels can be then formed into an array and packaged as indicated in block 230.

It has been found that glass syringe barrels exiting a Lehr oven at about 590° C. have satisfactorily low particulate levels on their surfaces to meet drug delivery device cleanliness standards. Test results have shown that barrels after heating at 590° C. for about 30 minutes have an average of 8.55 particles per barrel with a particle size of about 5–24 microns, with the barrels being substantially free of particles having a particle size of 25 microns or larger. Tests have also demonstrated that the syringe barrels have satisfactory sterility, toxicity and pyrogenicity levels as determined by standard testing procedures for drug delivery devices.

In embodiments of the invention, the syringes are preferably prefillable syringes as known in the art having an internal volume of about 0.3–60 ml. The syringe barrels 12 are made of glass suitable for long term storage of a drug solution.

Figure 7:
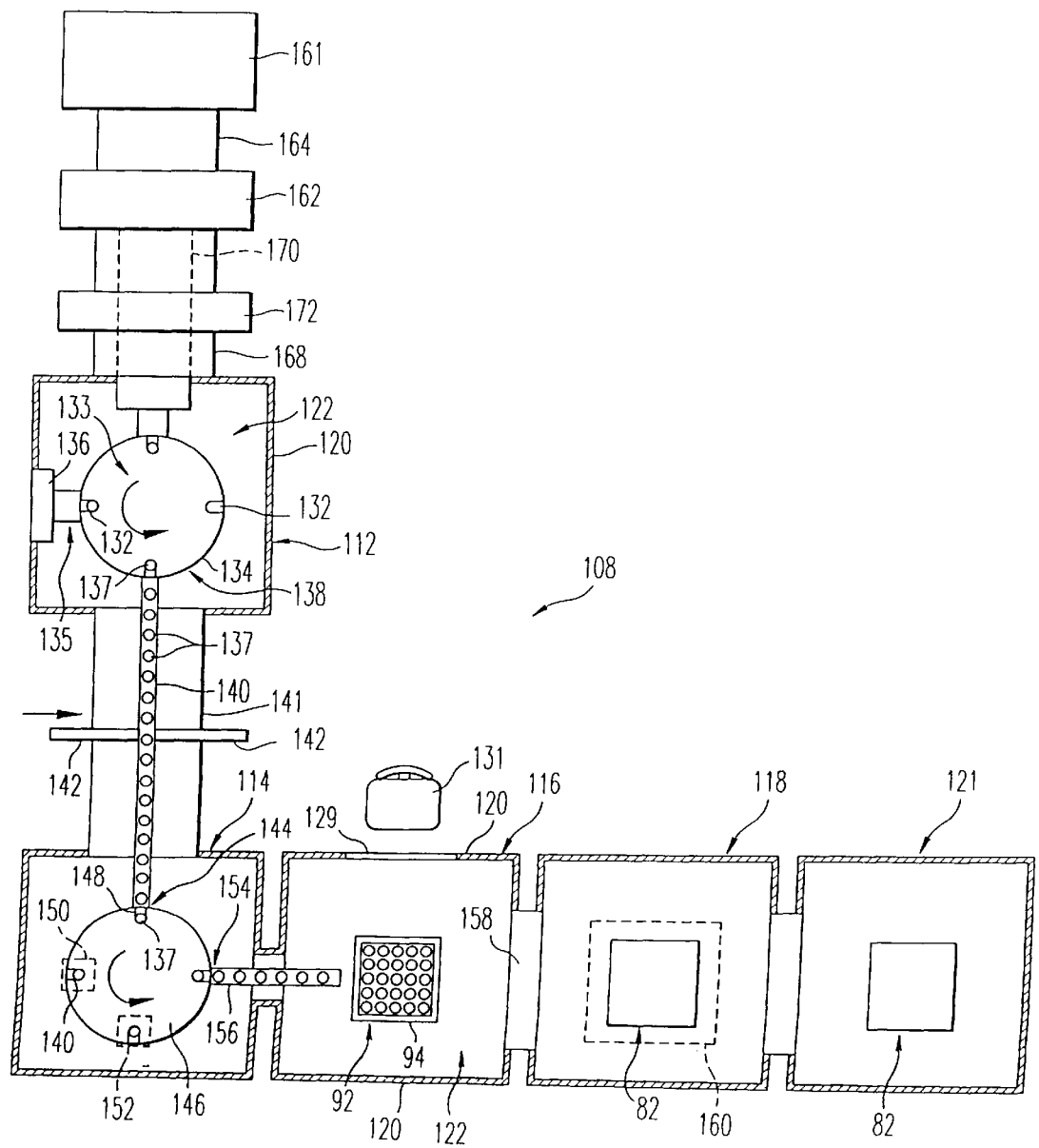
FIG. 7 is a top view of housing assemblies defining a locally controlled environment for cleaning, assembling and packaging syringe barrels in accordance with one embodiment of the invention.
Figure 8:
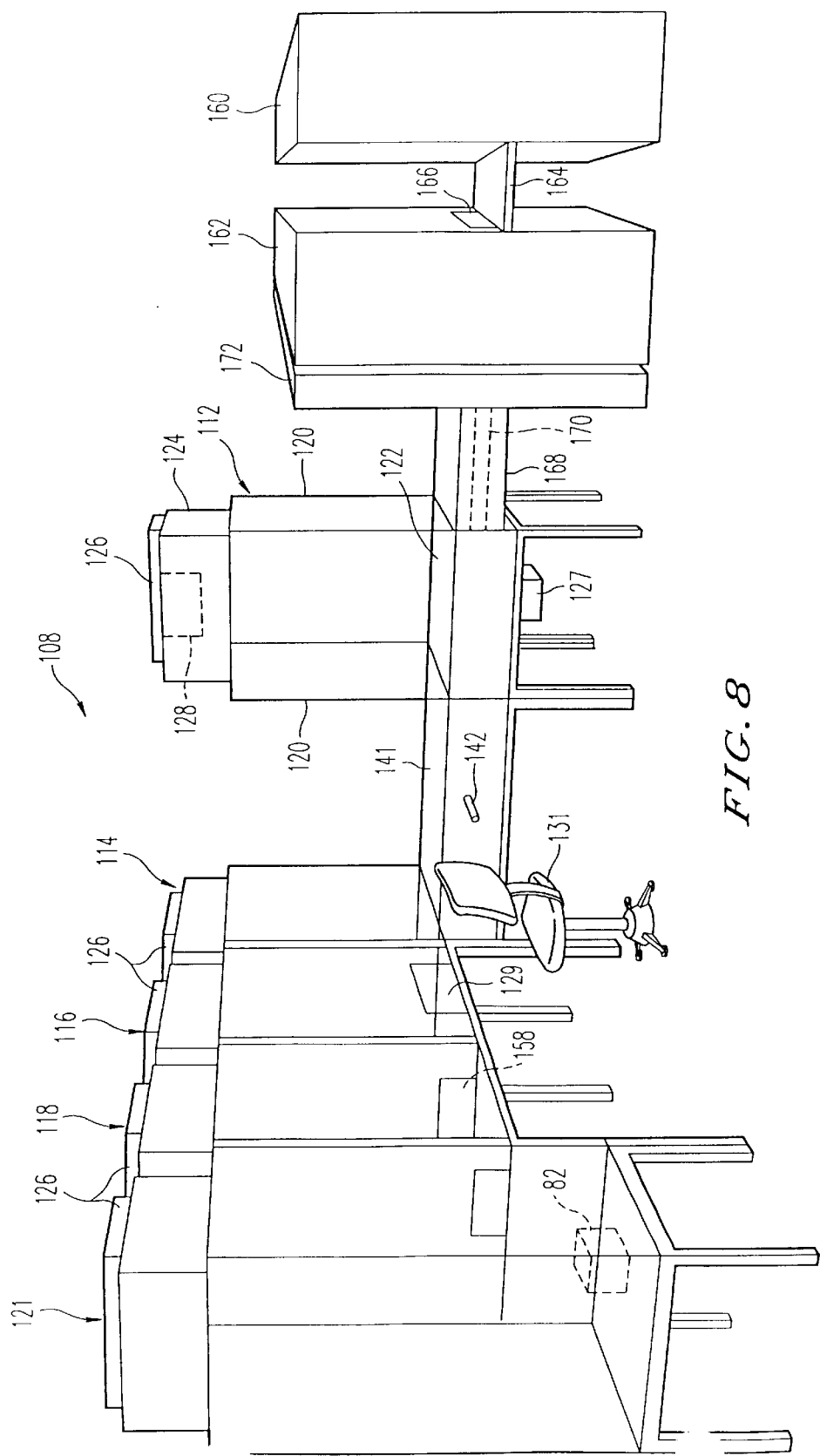
FIG. 8 is a perspective view of the locally controlled environment of FIG. 7.
Figure 9:
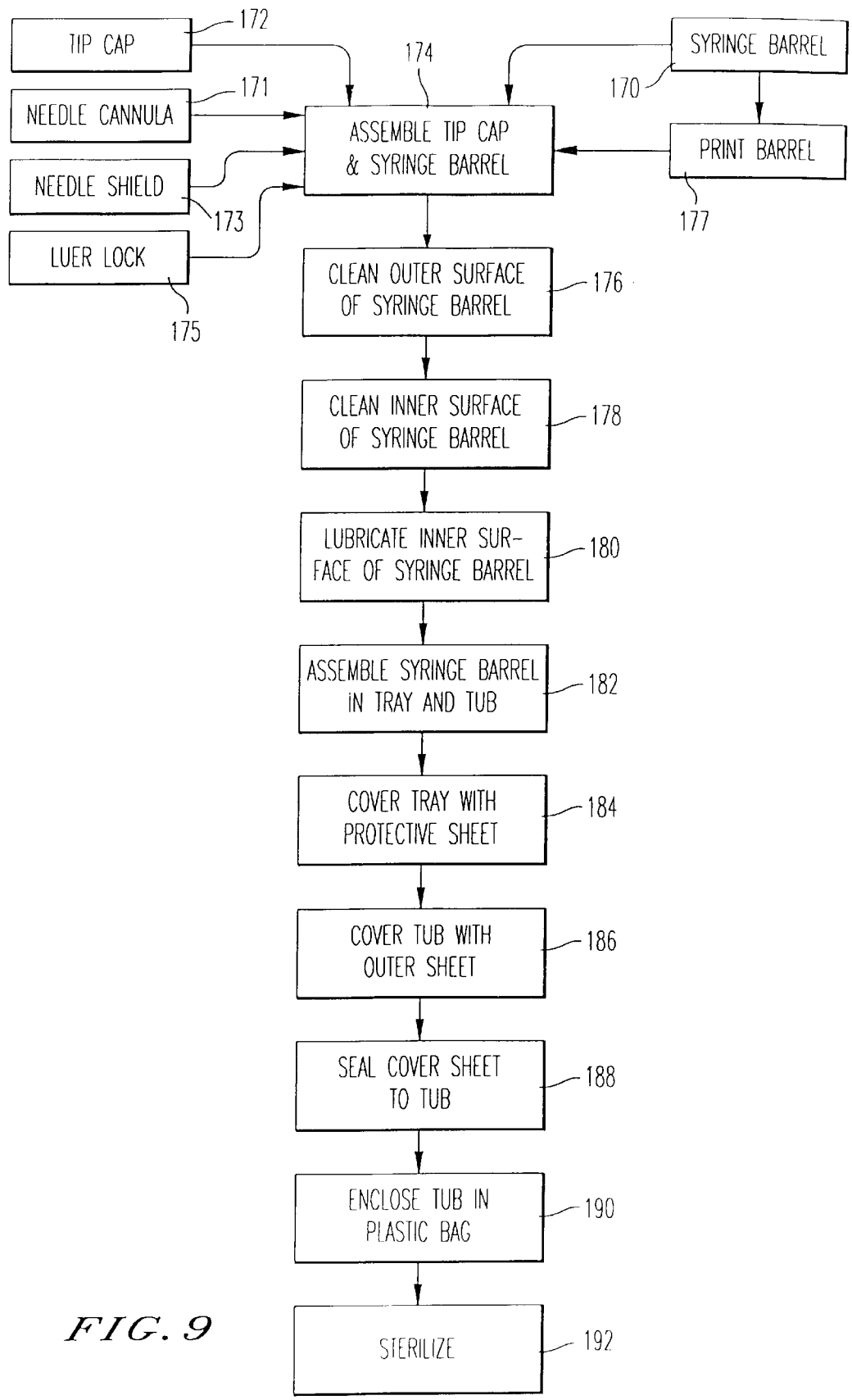
FIG. 9 is a flow chart of the assembly steps for packaging the syringe barrel assemblies.

In an embodiment of the invention, the syringe barrels and the barrel assembly tub package 84 are produced using an apparatus 108 depicted in FIGS. 7 and 8 by the method outlined in the flow charts of FIGS. 6 and 9. The apparatus 108 in the embodiment shown includes several modular housing assemblies 112, 114, 116 and 118 which are coupled together. Preferably, the housing assemblies are modular and portable so that they can be separated from one another for repair or replacement. In addition, modular assemblies permit expansion or reduction in overall size, as well as reconfiguration, to accommodate the particular needs of the overall operation. The modular housing assemblies can be coupled together directly or by intermediate housings or tunnels to prevent infiltration of unfiltered air.

The housing assemblies are substantially alike, although they can differ in size or shape to accommodate the specific assembly step being performed. For purposes of illustration, housing assembly 112 is shown which includes side walls 120, some or all of which may be made of glass or other transparent materials, completely surrounding a work space 122. It will be appreciated that housing assemblies 112, 114, 116 and 118 are substantially similar. A top member 124 is coupled to side walls 120 to enclose work space 122. Top member 124 has an air blower 126 and is coupled to a high efficiency particulate air filter (HEPA) 128 to direct filtered air into the housing assembly. Preferably, air blower 126 maintains a positive pressure in work space 122 to prevent infiltration of contaminated air. The efficiency of the HEPA filter determines the level of particulates and viable and non-viable particulates and pyrogens in the air in the work space 122. In a preferred embodiment of the invention, filter 128 removes particles of 0.3 microns or larger. In other embodiments, particles smaller than 0.3 microns can also be removed.

In one embodiment of the invention, the HEPA filters are selected to maintain the housing assemblies and the respective work spaces therein at levels meeting or exceeding Class 100 conditions with respect to particulates as defined by Federal Standard No. 209E, "Airborne Particulate Cleanliness Classes in Clean Rooms and Clean Zones", approved by the General Services Administration (Sep. 11, 1992). In other embodiments, the HEPA filters are selected to maintain cleanliness standards as needed which can be higher or lower than Class 100.

Air blower 126 directs clean filtered air downward through the housing assembly to an outlet (not shown) in the lower end of the housing assembly. An optional exhaust fan 127 can be included to draw air and any particulates or other contaminants out of the housing assembly. One or more of the side walls 120 can include an optional access opening 129 as shown in enclosure 116 to enable an operator to reach into the workspace and perform various operations. As shown in FIG. 7, a chair 131 or stool is provided for the operator. A positive pressure is preferably maintained in the workspace 122 to prevent air from entering through the access opening 129.

In the embodiment illustrated, the glass syringe barrels are formed in the glass forming apparatus 161 from glass cylinders. The formed glass syringe barrels are transferred to a Lehr oven 162 where the barrels are heated to at least 560° C. to anneal the glass and to relieve the stresses in the glass produced as a result of the barrel forming steps. The syringe barrel forming apparatus 160 is generally not enclosed in a clean area. The syringe barrels can be transferred directly to the Lehr oven 162 by a conveyor 164 passing through an opening 166 or the barrels can be transferred manually. In still further embodiments, the syringe barrels are transferred to a storage bin for a subsequent heating step in a Lehr oven.

After the glass syringe barrels are annealed in the Lehr oven 162, the syringe barrels exit through a tunnel 168 or other enclosure to maintain cleanliness and low bio-burden levels. In preferred embodiments, a conveyor 170 carries the finished glass barrels from the Lehr oven 162 through the tunnel 168 to the packaging and assembling apparatus 108. Alternatively, a robotic mechanism can be used to transfer the syringe barrels from a molding or annealing apparatus to a housing assembly. An optional printing apparatus 172 is provided downstream of the Lehr oven 162 to print indicia on the syringe barrel before assembling and packaging.

The housing assemblies shown in FIGS. 7 and 8 are coupled to an adjacent housing assembly in a manner to maintain a clean locally controlled environment. As shown, tunnel-like enclosures 141 are attached to the side walls 120 to carry the syringe barrels or other drug delivery devices from one housing assembly to another without exposure to outside air. An air blower and appropriate HEPA filter (not shown) can be provided in enclosure 141 as needed to maintain desired cleanliness levels.

Referring to FIG. 7, housing assembly 112 encloses an apparatus 133 for assembling the syringe barrels 12 with the selected component, such as a tip closure, needle cannula, Luer lock collar and needle sheath. The syringe barrels 12, which can be printed or unprinted, are essentially clean when fed directly from the Lehr oven 162. The syringe barrels are fed from the Lehr oven 162 or other supply to a recess 132 in a rotating table 134. Table 134 rotates to station 135 where clean components are fed from a supply entrance 136 and coupled to the ends of the syringe barrels 12 to produce a syringe barrel assembly 137 as shown in FIG. 1. The table 134 continues to rotate to station 138 where the syringe barrel assembly 137 is ejected onto a conveyor rail 140. Conveyor rail 140 is enclosed in a tunnel 141 to maintain the same cleanliness levels as in housing assembly 112. Preferably, the syringe barrel assemblies 137 are substantially clean and have a sufficiently low bio-burden so that further washing or cleaning steps can be eliminated. In embodiments where further cleaning is necessary, however, syringe barrel assemblies 137 are conveyed past nozzles 142 which direct streams of filtered, ionized air across the conveyor rail 140 to remove any particulates from the outer surfaces of syringe barrel assemblies 137 and to reduce static charge. Conveyor rail 140 has a discharge end 144 in housing assembly 114.

Housing assembly 114 contains a rotating table 146 having recesses 148 for receiving syringe barrel assemblies 137 from the conveyor rail 140. Table 146 rotates to carry the syringe barrel assemblies 137 to a cleaning station 150 where streams of filtered, ionized air are directed into the syringe barrel assemblies 137 to loosen and remove any particulates from their inner surfaces while a vacuum is applied to the inner surface to carry the particulates away. In preferred embodiments, the manufacturing process produces sufficiently clean syringe barrels so that this cleaning step is optional. Thereafter, table 146 rotates to carry the syringe barrel assemblies 137 to a lubricating station 152 where a thin coating of a lubricant is applied to the inner surface of the syringe barrel assemblies 137. The lubricant is preferably a silicone oil as known in the art. Table 146 then rotates to carry the syringe barrel assemblies 137 to a discharge station 154, where the syringe barrel assemblies 137 are discharged onto a conveyor rail 156 and conveyed to housing assembly 116.

In the embodiment illustrated, housing assembly 116 includes an access opening 129 in side wall 120 to enable an operator sitting on a seat or chair 131 to reach into the housing assembly 116. The opening 129 is dimensioned to enable the operator to perform various manual operations while maintaining the workstation area at the desired cleanliness level. In the embodiment illustrated, the operator examines the syringe barrel assemblies 137 and places the assemblies in the tray 84 which is in the tub 92. The operator then places the protective sheet material 102 over the syringe barrel assemblies 137. The closure sheet 104 is then placed over the tub 92 and the tub is manually placed in housing assembly 118 through an opening 158 in side wall 120. In further embodiments, the syringe barrel assemblies 137 are placed in tub 92 automatically by suitable machinery.

Within housing assembly 118 is a heated platen 160 for heat sealing the closure sheet 104 onto tub 92. The platen 160 is lowered onto the sheet 104 and the sheet is sealed to the flange 100 of the tub 92 to enclose the syringe barrel assemblies 137. Since the syringe barrel assemblies 137 are now enclosed in protective packaging, the tub can be removed from the housing assembly 118 without the risk of contamination of the syringe barrel assemblies 137. The tub can then be sealed in a plastic bag or other protective outer wrap and placed in suitable shipping cartons. Standard heat sealing and bagging devices are typically used.

Alternatively, the tub package 82 can be transferred from the housing assembly 118 to a further housing assembly 121 serving as a sterilization chamber. Sterilization can be, for example, by gamma or beta radiation, hot air or steam autoclave. In preferred embodiments, the cover sheet 104 is a gas permeable material which is permeable to ethylene oxide sterilizing gas. Typically, the tub package 82 is exposed to ethylene oxide for sufficient time to permeate the closure sheet and sterilize the contents thereof. The chamber is then evacuated and purged with carbon dioxide or other gas to remove the ethylene oxide. The plastic bagging operation described above may then be performed.

In the embodiment illustrated in FIG. 7, sterilization chamber 121 is connected in line with housing assembly 118 to receive the tub package 82. Alternatively, the tub packages 82 are transferred to a sterilization chamber at a different location. Sterilization can also be performed after placing the packages 82 in suitable shipping cartons.

The apparatus of FIG. 7 is intended to be exemplary of one embodiment of the invention. In this embodiment, the housing assemblies define different work stations and are in modular form for assembly and disassembly. In further embodiments, apparatus 108 can be a single housing enclosing all of the work stations.

Referring to FIG. 9, a flow chart depicts the method of assembly of the tub package 82. Clean syringe barrels are fed from a supply as indicated in block 170, and clean tip closures are fed from a supply as indicated in block 172. The syringe barrels can be fed to an optional print station as indicated in block 177. Optional needle cannulas as indicated in block 171, needle shields as indicated in block 173 and Luer lock collars as indicated in block 175 are also fed from a supply. The syringe barrels and syringe components are supplied to a locally controlled environment for assembly of the components to the syringe barrels indicated in block 174. The syringe barrel and tip closure assemblies are conveyed through an optional stream of clean, ionized air to remove particulates from the outer surface of the syringe barrel assemblies as indicated in block 176. The syringe barrel assemblies are then passed to a station where the inner surfaces of the syringe barrels are cleaned with filtered, ionized air and vacuum as indicated in block 178, and to a lubricating station where a lubricant is applied to the inner surfaces as indicated in block 180.

The lubricated syringe assemblies are placed in the tray and tub as indicated in block 182, followed by the addition of a protective sheet as indicated in block 184 and an outer cover sheet as indicated in block 186. The tub package is then placed in a heat sealer to seal the cover sheet to the tub as indicated in block 188. The sealed tub is enclosed in a plastic bag as indicated in block 190, followed by sterilization as indicated in block 192.

In a further embodiment, a housing assembly substantially as described above encloses a container filling device for filling the medical container with the desired substance. The container can be a suitable medical container such as a vial or syringe barrel. The housing assembly includes an inlet for receiving the container and an air or water wash device as needed for cleaning the container. The filling device fills the clean containers and attaches a suitable closure to close the container. The cleaning, filling and assembling devices can be enclosed in a single housing assembly or enclosed in separate housing assemblies connected together in series by chutes, tunnels or other enclosures. The drug containers can be molded plastic or formed glass which are captured immediately after molding or forming in the housing assembly to maintain the clean and low bio-burden levels. The molding and forming devices can be positioned next to the housing assembly and connected thereto by a closed conveyor, tunnel or chute. In further embodiments, the molding or forming device can be enclosed in a housing assembly to define an environmentally controlled area to maintain cleanliness standards.

The package 82 of syringe barrel assemblies and the packaged stoppers can be transferred to an enclosed housing assembly for filling the syringe barrel and assembling a prefilled syringe. Each syringe barrel is filled with a predetermined amount of a substance while held in a closed, clean containment area. The containment area is then evacuated and the plunger and stopper assembly is positioned in the open end of the syringe barrel. The vacuum is then released and the plunger is drawn into the syringe barrel by the vacuum remaining within the barrel. Alternatively, the plunger and syringe barrel can be assembled by a vent tube stoppering process as known in the art. Thereafter, the assembled syringes are packaged as prefilled syringes and sold for use by health care providers.

Figure 10:
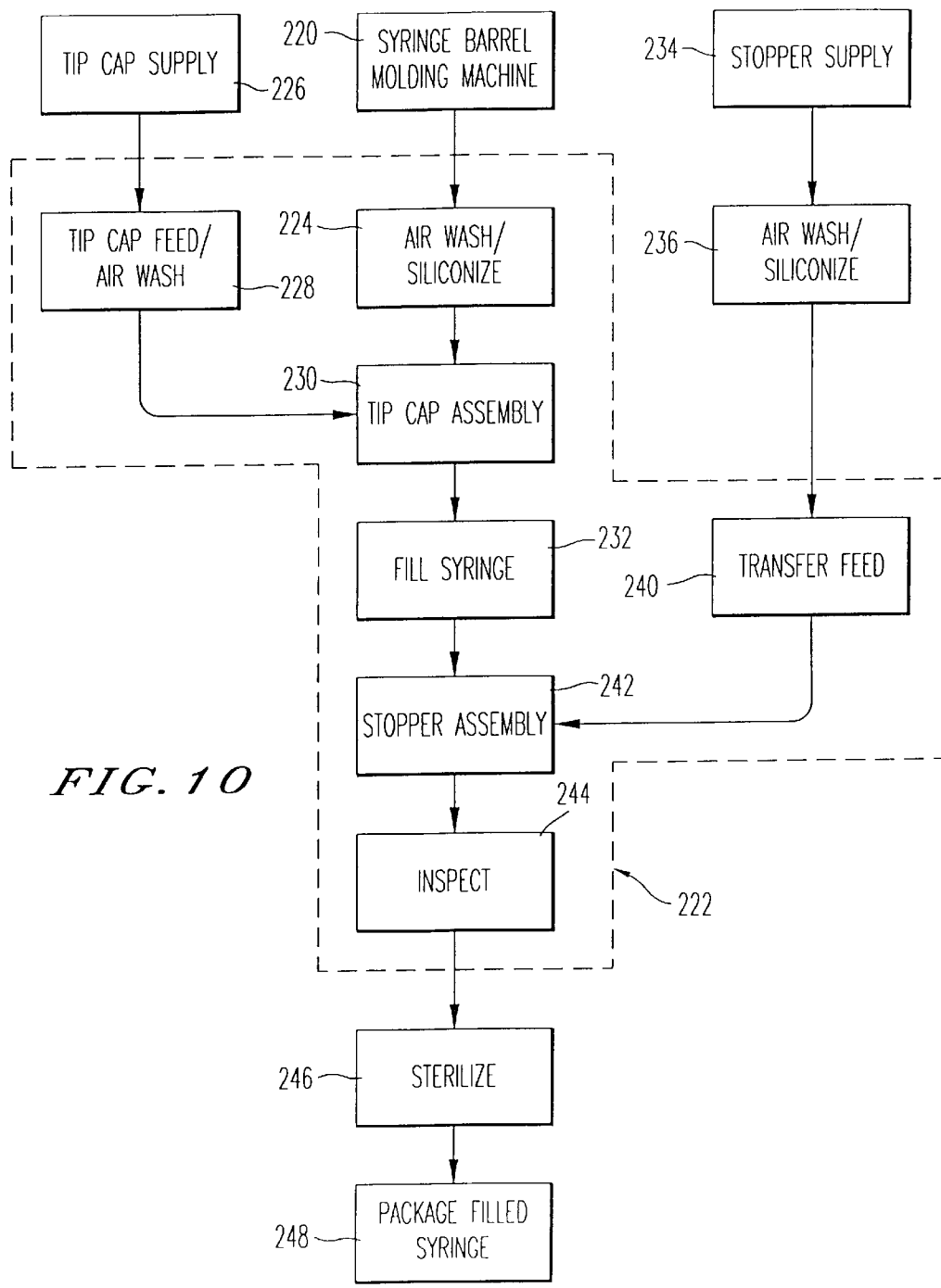
FIG. 10 is a flow chart of the filling steps for filling syringe barrels to produce prefilled syringes.

FIG. 10 illustrates a flow chart for a method of producing a prefilled syringe. Referring to FIG. 10, a supply of preformed syringe barrels are formed in a syringe barrel molding machine indicated by block 220. The molded syringe barrels are transferred into a locally controlled environment indicated by 222 preferably without any additional cleaning or sterilizing steps. It is preferred that the transferring of molded syringe barrels to the locally controlled environment be immediate. The syringe barrels are washed with air to remove particulates and coated with a lubricant such as silicone lubricating oil on the inner surface as indicated by block 224. A supply of tip caps indicated by block 226 is fed into the locally controlled environment 222. The tip caps are air washed as indicated by block 228. The cleaned tip caps and syringe barrels are conveyed to an assembly device indicated by block 230 where the tip caps are assembled onto the syringe barrel to close the tip or nozzle of the syringe barrel. The syringe barrel assemblies are then conveyed to a filing station indicate by block 232 where the syringe barrel is filled with a substance as defined herein.

A supply of stoppers indicated by block 234 is transferred to a washing station indicated by block 236 where a silicone lubricant is applied to the stoppers. The lubricated stoppers are then delivered to a transfer feed device indicated by block 240 within the locally controlled environment 222. The stoppers are then assembled with the filled syringe barrels indicated by block 242 to close the syringe. In particular, the stopper is inserted into the open proximal receiving end of the syringe barrel. The prefilled syringes are preferably inspected for defects as indicated by block 244 and discharged form the locally controlled environment 222, sterilized as indicated by block 246 and packaged either individually or in bulk for transporting indicated by block 248. Suitable sterilization methods include heat, steam, radiation and gas sterilization as known in the art. In some uses, for example, if the syringe is to be used in a surgical procedure, the sterilization step should occur after the syringe is packaged. It is also within the purview of the present invention to include sterilization of the syringe both before and after packaging.

In the method of FIG. 10, the syringe barrels are breach filled and the tip cap is coupled to the barrel before filling. It will be understood by those skilled in the art that a stopper and/or syringe plunger can be coupled to the syringe barrel before filling and the syringe barrel filled through the tip or nozzle. Thereafter, a tip cap or needle can be attached to the filled syringe barrel to close the tip. Accordingly, medical containers such as the syringe can be filled by known filling methods. Exemplary methods for filling syringes and other medical containers are disclosed in U.S. Pat. No. 5,620,425 to Hefferman et al., U.S. Pat. No. 5,597,530 to Smith et al., U.S. Pat. No. 5,537,042 to DeHaen, U.S. Pat. No. 5,531,255 to Vacca, U.S. Pat. Nos. 5,519,984 and 5,373,684 to Veussink et al., U.S. Pat. No. 5,256,154 and 5,287,983 to Liebert et al. and U.S. Pat. No. 4,718,463 to Jurgens, Jr. et al., which are hereby incorporated by reference in their entirety.

The locally controlled environment of the illustrated embodiments includes assembly machinery for producing bulk packaging of syringe barrel assemblies, filling syringe barrels to form prefilled syringes and to produce prefilled drug containers. It will be appreciated that other medical containers can be assembled, constructed or packaged in the locally controlled environment. Examples of containers which can be packaged including various drug containers, vials, ampoules or other containers where a clean environment is required during the processing step. In addition, the cleanliness standard for the locally controlled environment is determined by the air filtration system to obtain a sufficiently low particulate and pyrogen level as required. In the embodiment disclosed, the HEPA filters are sufficient to maintain a Class 100 cleanliness standard in each of the housing assemblies. In further embodiments, the HEPA filters can be selected to attain Class 10, Class 10,000 or Class 100,000 cleanliness conditions.

Figure 11:
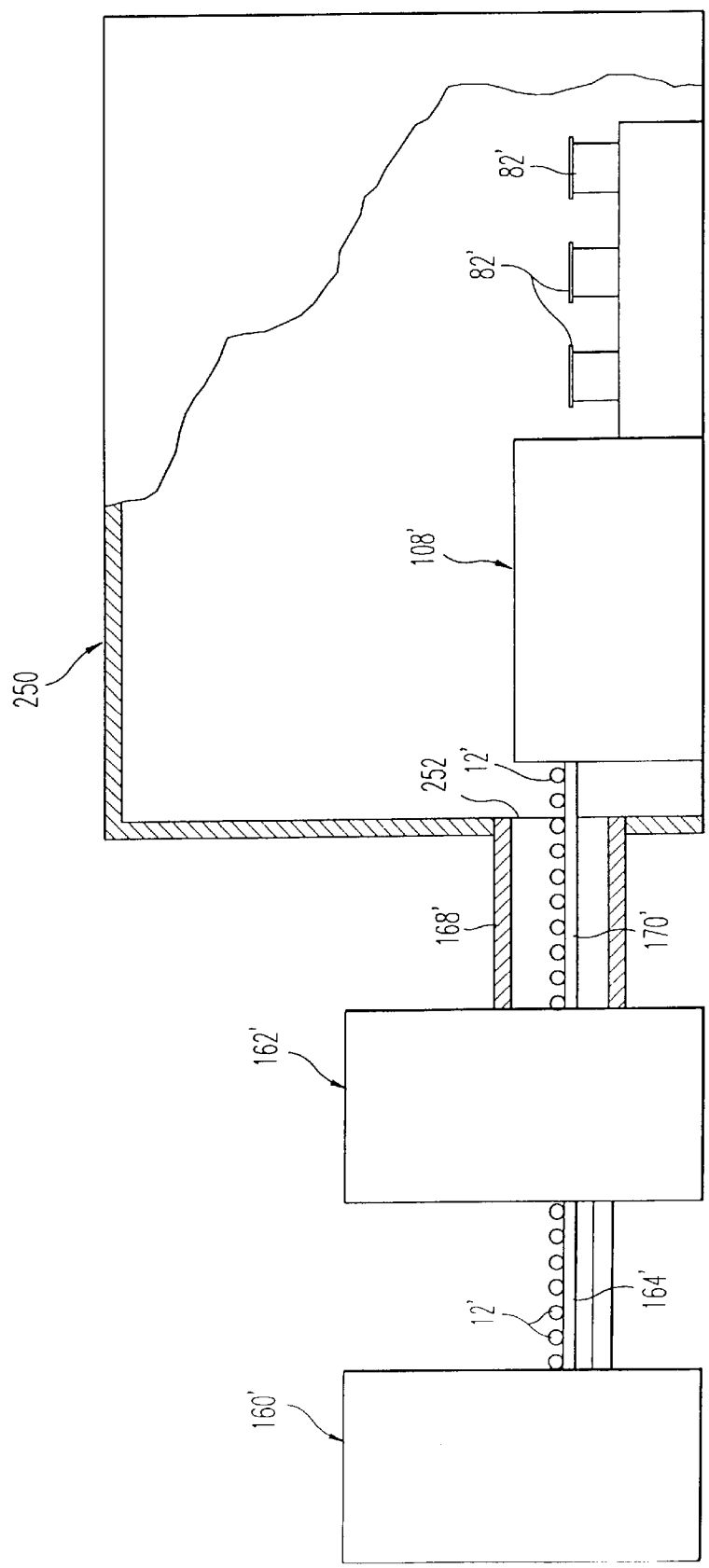
FIG. 11 is a side elevational view of a glass forming and glass annealing apparatus coupled to a clean room for assembling and packaging the syringe barrels in accordance with another embodiment of the invention.

FIG. 11 illustrates a second embodiment of the manufacturing and packing of medical appliances. The assembly is similar to the embodiment of FIG. 8 except that assembly and packaging apparatus 108' is contained in a clean room 250. In this embodiment, similar components are identified by the same reference number with the addition of a prime. Glass syringe barrels 12' are manufactured in a glass forming apparatus 160'. The syringe barrels 12' are conveyed by conveyor 164' to an annealing oven 162'. A closed tunnel 168' supporting a conveyor 170' delivers the syringe barrels 12' to a clean room 250. The clean room can be a standard clean room having suitable air blowers, HEPA filters, temperature and antistatic controls to maintain the cleanliness levels within prescribed limits determined by the selected class.

The glass syringe barrels are conveyed through an opening 252 in the clean room 250 and delivered to the assembly and packaging apparatus 108'. The syringe barrels can be further cleaned, assembled with syringe components and packaged in trays and tubs as in the previous embodiment. Optionally, the syringe barrels can be filled to produce prefilled syringes before packaging. The packaged syringe barrels 82' are then placed in cartons or other shipping containers for shipping to the ultimate consumer. It will be understood molded plastic drug containers can be molded and captured immediately after molding in a similar clean room where the drug containers can be filled and/or packaged.

Although certain embodiments have been selected to illustrate the invention, it will be apparent to one skilled in the art that other embodiments can be used without departing from the scope of the invention. For example, processes within the scope of the invention can be used with either glass or plastic syringe barrels through the changing of conditions to accommodate the requirements of glass or plastic while still following the process steps.

What is claimed is:

1. A method of producing a prefillable syringe comprising the steps of:

forming a plurality of clean syringe barrels in a glass forming device for shaping a cylindrical glass tube into syringe barrels having a first open end for receiving a syringe plunger and a second open end for discharging contents from said syringe barrel, transferring said syringe barrels to an environmentally controlled area to maintain a predetermined cleanliness level, and cleaning said syringe barrels by directing a filtered air stream to loosen particulates from at least one surface of said syringe barrels and applying a vacuum to remove said loosened particulates from said syringe barrels within said environmentally controlled area.

2. The method of claim 1, further comprising the steps of:

enclosing said syringe barrels in a container, and sterilizing said container.

3. The method of claim 2, wherein said sterilizing step comprises exposing said container to either gamma radiation, beta radiation, ethylene oxide, hot air, steam or a sterilizing gas.

4. The method of claim 1, wherein said method comprises heating said syringe barrels to an annealing temperature to simultaneously anneal and clean said syringe barrels.

5. The method of claim 1, further comprising the step of enclosing said forming device in a locally controlled area to maintain a predetermined cleanliness level.

6. The method of claim 1, further comprising the steps of forming an array of said syringe barrels, placing said array in a container, and closing and sealing said container to form packaged syringe barrels.

7. The method of claim 6, further comprising the step of positioning a protective sheet over said array of syringe barrels in said container before applying a cover sheet to said container to seal said container.

8. The method of claim 6, further comprising the step of applying a coating of a lubricant to an inner surface of said syringe barrel.

9. The method of claim 1, further comprising the steps of applying a tip cap to close said second open end of said syringe barrel, filling said syringe barrel with a substance, applying a stopper to said first open end of said syringe barrel to form a prefilled syringe.

10. The method of claim 9, wherein the step of filling said syringe barrel with the substance including a substance selected from the group consisting of saline solutions, flush solutions or contrast agents, pharmaceutical agents and vaccines, in either a dry or liquid state.

11. The method of claim 1, wherein said air stream comprises ionized air.

12. The method of claim 1, wherein said forming step includes forming said syringe barrel by heating a glass tube to a temperature of about 760° C. to 1100° C.

13. The method of claim 12, further comprising the step of annealing said syringe barrel at a temperature of at least about 560° C.

14. The method of claim 12, wherein said forming step comprises heating a first end of said glass tube to a temperature whereby said glass tube is pliable and shaping said first end to form a flange extending substantially radially outward from a center axis of said glass tube.

15. The method of claim 14, further comprising the steps of heating a second end of said glass tube to a temperature whereby said glass tube is in a pliable state and shaping said second end for receiving a cannula needle.

16. The method of claim 14, wherein said forming step includes heating a second end of said glass tube to a temperature whereby said glass tube is in a pliable state and shaping said second end into a nozzle tip for receiving a needle, and further comprising the step of securing a needle in the nozzle tip by an adhesive.

17. The method of claim 16, further comprising the step of coupling a protective plastic needle sheath having an open end with said nozzle tip, said protective plastic needle sheath having a hollow, substantially cylindrical shape and being dimensioned to receive said needle so that said protective plastic needle sheath contacts and closes off a tip of the needle to prevent leakage.

18. The method of claim 1, wherein said environmentally controlled area maintains a cleanliness level of about Class 100.

19. The method of claim 1, wherein said environmentally controlled area comprises at least one housing assembly having an air blower and a HEPA filter coupled to said air blower to filter air entering said at least one housing assembly.

20. The method of claim 13, wherein said at least one housing assembly is maintained at a positive internal pressure to prevent unfiltered air from entering said housing assemblies.

21. The method of claim 1, further comprising the steps of providing a plurality of collars to said environmentally controlled area; and snapping each said collar to said second open end of each syringe barrel.

22. A method of producing prefillable syringe barrel assemblies in one or more housing assembly for maintaining a predetermined cleanliness level comprising the steps of:

forming a plurality of clean syringe barrels in a forming device, said syringe barrels each having a first open end for receiving a syringe plunger and a second open end for discharging contents from said syringe barrels, with the second open end being formed into a nozzle tip for receiving a needle;

supplying a plurality of needles and securing said needles in the nozzle tips of said syringe barrels by an adhesive;

supplying a plurality of protective plastic needle sheaths and coupling the protective plastic needle sheaths to said nozzle tips of said syringe barrels to form syringe barrel assemblies;

transferring said syringe barrel assemblies to at least one housing assembly for maintaining a predetermined cleanliness level;

directing a filtered air stream to loosen any particulates from at least one surface of said syringe barrels assemblies and applying a vacuum to remove loosened particulates from said syringe barrel in said at least one housing assembly transferring said syringe barrel assemblies to at least another housing assembly; and packaging at least one or more of said syringe barrel assemblies in a package in said at least another housing assembly.

23. The method of claim 22, wherein said step of forming said syringe barrels comprises supplying a cylindrical glass tube to said forming device and heating said first open end of said glass tube to a temperature whereby said glass tube is pliable and forming a flange about said first open end and heating said second open end of said glass tube to a temperature whereby said glass tube is pliable and forming said nozzle tip at said second open end.

24. The method of claim 23, wherein said protective plastic needle sheaths each have a hollow, substantially cylindrical shape and are dimensioned to receive said needle, and said coupling step includes contacting protective plastic needle sheaths with said needle so that said protective plastic needle sheath closes off a tip of each of the needles to prevent leakage.

25. The method of claim 23, further comprising the step of filling said syringe barrels with a desired substance and coupling a closure member to said syringe barrels to close said first open ends of said syringe barrels.

26. The method of claim 22, wherein said air stream comprises ionized air.

27. The method of claim 22, further comprising the steps of filling each said syringe barrel with a substance selected from the group consisting of saline solutions, flush solutions or contrast agents, or pharmaceutical agents and vaccines, in either a dry or liquid state and coupling a closure member to said syringe barrels to close the first open ends of said syringe barrels.

28. The method of claim 22, further comprising the step of sterilizing said package in at least another housing assembly.

29. The method of claim 45, wherein said packaging step includes forming an array of said syringe barrel assemblies, and placing said array in a container having a closed bottom, side walls and an open top end, applying a cover sheet to said container to entirely close said container, and sealing said cover sheet to said container.

* * * * *